United States Patent
Millan

(10) Patent No.: US 6,854,717 B2
(45) Date of Patent: Feb. 15, 2005

(54) EVAPORATOR DEVICE FOR ACTIVE SUBSTANCES

(75) Inventor: Jordi Basagañas Millan, Barcelona (ES)

(73) Assignee: DBK Espana, S.A., Barcellona (ES)

( * ) Notice: Subject to any disclaimer, the term of this patent is extended or adjusted under 35 U.S.C. 154(b) by 0 days.

(21) Appl. No.: 10/730,741

(22) Filed: Dec. 4, 2003

(65) Prior Publication Data

US 2004/0145067 A1 Jul. 29, 2004

Related U.S. Application Data

(63) Continuation of application No. PCT/ES02/00180, filed on Apr. 12, 2002.

(51) Int. Cl.$^7$ .................................................. B01F 3/04
(52) U.S. Cl. ........................ 261/26; 261/107; 261/142; 261/DIG. 88; 261/DIG. 89; 422/123; 392/392; 392/395
(58) Field of Search .................... 261/26, 107, 142, 261/DIG. 65, DIG. 88, DIG. 89; 423/123; 392/390, 392, 395; 219/209; 422/123

(56) References Cited

U.S. PATENT DOCUMENTS 5,175,791 A * 12/1992 Muderlak et al. ........... 392/390
6,097,881 A 8/2000 DeWitt et al.
6,278,840 B1 8/2001 Basaganas Millan
6,285,830 B1 9/2001 Basaganas Millan
2002/0159916 A1 * 10/2002 Whitby et al. .................. 422/4
2003/0194355 A1 * 10/2003 Pedrotti et al. ............. 422/124
2004/0033171 A1 * 2/2004 Kvietok et al. ............. 422/123

FOREIGN PATENT DOCUMENTS

| EP | 0 689 766 | 1/1996 |
| EP | 0 976 410 | 2/2000 |
| EP | 1 055 430 | 11/2000 |
| ES | 1 040 060 | 3/1999 |
| ES | 2 137 111 | 12/1999 |
| WO | 00/10617 | 3/2000 |
| WO | 01/68154 | 9/2001 |

* cited by examiner

Primary Examiner—Robert A. Hopkins
(74) Attorney, Agent, or Firm—Katten Muchin Zavis Rosenman

(57) ABSTRACT

The device comprises a base (1) and an exchangeable case (7), between which are placed corresponding components such as a bottle (9) containing the fragrant liquid and the corresponding wick (8), as well as the heating elements (4) connected to corresponding metallic contacts (5) and mounted on a support (3), also including a platform or printed circuit (2) with electronic components that allow optimizing the diffusion of the fragrance, to prevent olfactory saturation of the user, independently of the manual actuation means that allow regulating the intensity of evaporation of the fragrant liquid itself. The device also includes the corresponding plug (10) placed in correspondence with the part near the bottom end of the base (1).

10 Claims, 3 Drawing Sheets

EVAPORATOR DEVICE FOR ACTIVE SUBSTANCES

CROSS-REFERENCE TO RELATED APPLICATION

The present application is a continuation of International Application No. PCT/ES02/00180 which was filed on Apr. 12, 2002.

OBJECT OF THE INVENTION

The present invention relates to an evaporator device for active substances having structural and functional characteristics providing various and remarkable advantages compared to the existing and known devices for the same purposes.

The object of the invention is to provide an evaporator device for active substances that includes a minimum number of parts, with the corresponding savings in its manufacture and assembly, which can be performed in a fully automated manner. In addition, the device includes electronics that allow controlling the diffusion of the active substances. It also allows regulating the intensity of the evaporation by a mechanical actuation operated at will by the consumer or user.

BACKGROUND OF THE INVENTION

There are many evaporator devices for active substances used as air fresheners based on heating with the corresponding resistors of a fragrant liquid contained in a vessel with an emerging wick, so that the heat causes the evaporation of the liquid that impregnates the wick resulting in the corresponding diffusion of the fragrance.

This type of devices generally suffer from a series of drawbacks and disadvantages such as a large size, a large number of parts responsible for said size, and the use of wires to establish the corresponding internal electrical contacts, all of which cause a complicated and slow assembly.

In addition, known devices include a corresponding plug placed in an approximately intermediate area of the casing, so that when used on double sockets, as is frequent, both sockets are covered thereby preventing the use of the theoretically free socket, the other one being used by the plug of the evaporator device.

Furthermore, known devices can be regulated to increase or decrease the evaporation, or even allowing their deactivation if they overheat or if there is an excessive evaporation of the fragrant product.

DESCRIPTION OF THE INVENTION

The device taught is not only designed to solve the above-described drawbacks but also to provide hitherto unknown performances implying a technological advance in the field of this type of evaporator devices.

More specifically, the device of the invention includes as one of its characteristics a printed circuit with the corresponding electronics to optimize the diffusion of the fragrance without causing the olfactory saturation of the user, by which is meant the physiological phenomenon taking place by adaptation or fatigue of the olfactory sensory receptors (with the corresponding inhibition of the sensory input signals and deactivation of the brain mechanisms associated to conscious perception) to a specific odor, which occurs after a prolonged exposure to a given olfactory stimulus.

In this sense, the object of the invention by virtue of the electronics it incorporates allows controlling the diffusion of the fragrance by providing a program of on/off cycles predetermined by the manufacturer that is not perceivable nor manipulable by the user, in order to increase the olfactory perception of the user and optimize the emitted fragrance, so that a better performance is obtained with less liquid; in other words it allows using bottles containing less liquid and therefore smaller and less costly, allowing an improved performance for the user.

The electronic platform that constitutes the printed circuit allows one or more functionalities in addition to the basic one, the aforementioned cycles program, among which can be mentioned the incorporation of a light sensor for its automatic activation in the presence of light, as well as an operation indicator and even an ornamental illumination for the bottle containing the liquid, or an on/off button allowing the user to manually turn it on/off at will.

In addition, also a novel characteristic of the evaporator of the invention is the fact that its architecture is conceived to allow its assembly in fully automated production lines, with a high production rate and demanding quality standards, preventing manual handling and the associated "non-quality" risks, so that in addition to having a fully automated assembly process the structure is considerably simplified as the component elements are associated by superposition, in a sandwich type assembly, allowing to assemble the components consecutively on each other by simple movements of robotic arms.

Specifically, the architecture or structure of the device includes the general and protective case, the printed circuit with the corresponding electronics, the metal contacts and resistances forming an assembly integrated in the electronics platform, an intermediate wall enclosing all of the above components and a case complementing the corresponding bottle support case with the liquid and wick, so that the latter case determines a means embellishing the whole of the device and can be interchangeable in the factory providing a great flexibility of aesthetic design of the assembly, allowing multiple appearances of the device with a minimal impact in the industrialization process.

Finally, as regards the heating system incorporated by the device, it consists of vertically arranged metal-oxide resistors that allow a more efficient heat transmission to the wick placed at the bottle mouth, said heating system being fully integrated in the device assembly (inserted in the printed circuit containing the electronic control system), thereby allowing to reduce the number of components in addition to reducing the cost of assembly.

The device also includes manual actuation means for regulating the evaporation intensity, allowing the device to reach the market either with the traditional components only or, without any variation, with the aforementioned electronics (with the combinations of the various options: light sensor, operation indicator, on/off button and ornamental bottle lighting).

The mechanism comprising the manual actuation means for regulating the evaporation intensity is independent of the electronics optimizing the diffusion of the active substance, as the former can be operated at will by the user, while the electronics is inaccessible to the user.

DESCRIPTION OF THE DRAWINGS

To complement the description being made and in order to aid a better understanding of the characteristics of the invention according to an example of preferred embodiment, the description is accompanied by a set of drawings forming an integral part of it in which, for purposes of illustration only and in a non-limiting sense the following is shown.

PREFERRED EMBODIMENT OF THE INVENTION

Figure 1:
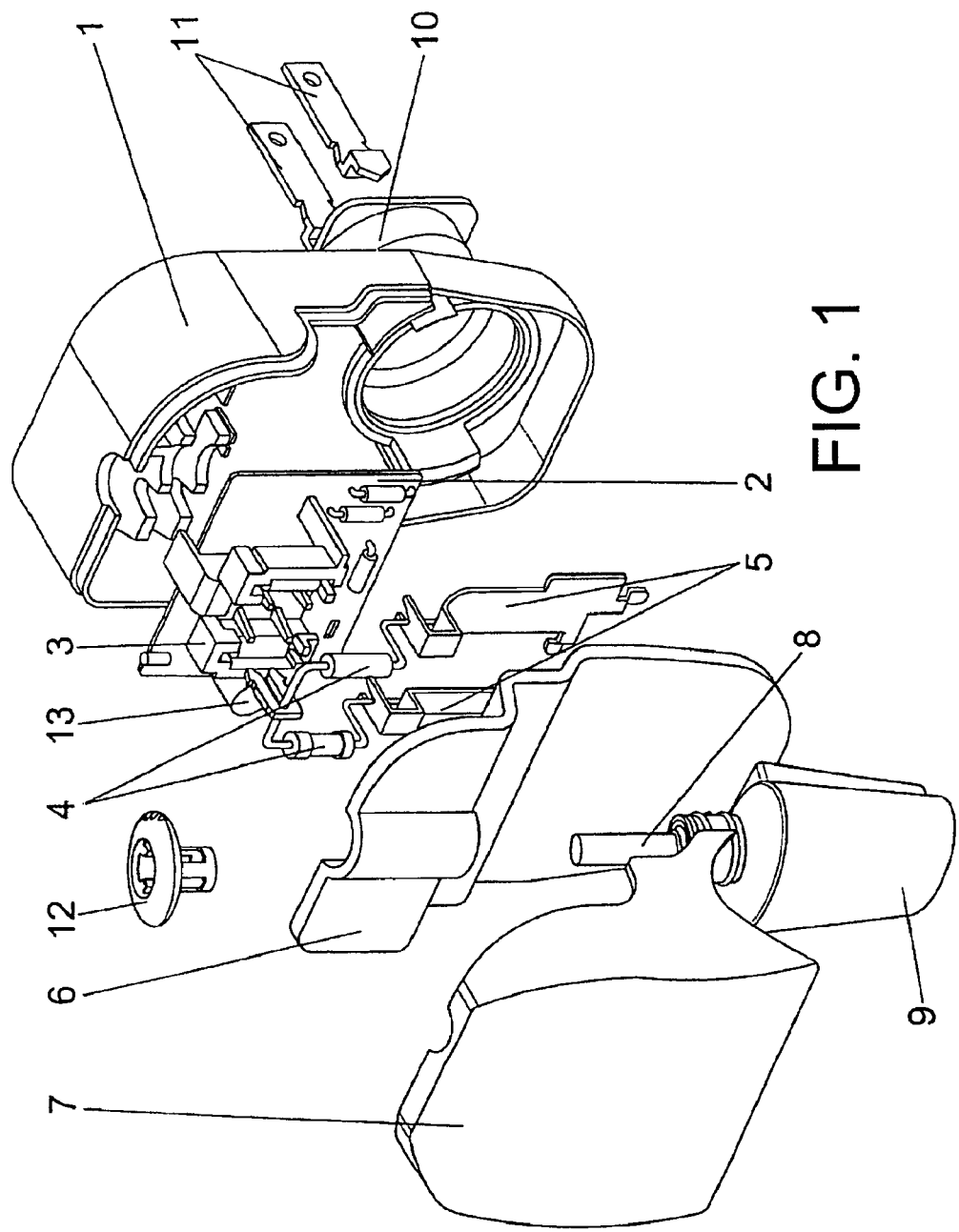
FIG. 1 shows a general exploded view in perspective of the various parts or components constituting the general architecture of the evaporator device for active substances, made according to the object of the invention.
Figure 2:
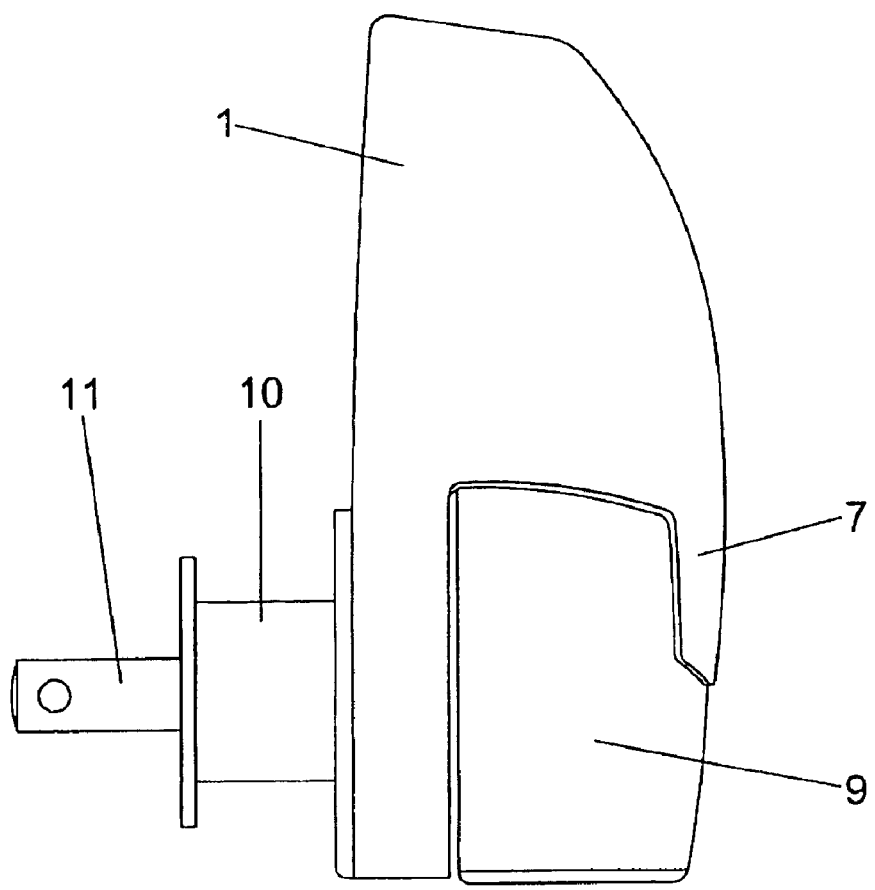
FIG. 2 shows a side elevation view of the evaporator device made according to the object of the invention, this is, with the components shown in the previous figure properly assembled allowing to see the inferior position of the corresponding device plug.

In view of the described figures, the device of the invention can be seen to include a base (1) for assembling the various components, which consist of a printed circuit board (2) with a support (3) for the heating resistors (4) connected to the corresponding metallic contacts (5), replacing the conventional wires used for the same purpose, all of it housed inside the base (1) and closed by the piece (6) in the form of walls, all of it complemented by a casing (7) that is placed on the front and is exchangeable, providing a great flexibility of aesthetic design of the device assembly, as the casing (7) can have multiple appearances.

The heating resistors (4) shall be made of metal oxide and are vertically arranged, allowing a greater efficiency in heat transmission to the wick (8) emerging from the bottle (9) containing the fragrant liquid, the bottle (9) being placed on the base (1), such that this bottle (9) has a mainly flat and compact configuration allowing a significant reduction of the volume, while the heating resistors (4), as can be seen in FIG. 1, are integrated in the device, thereby allowing to reduce the number of components as well as the cost of assembly.

From the base (1) emerges the corresponding plug (10) with its pins (11), such that the plug (10) is placed in correspondence with the lower part of the device assembly, so that when it is connected one socket of a double socket base the other socket remains free to be used, while if it is connected to the other socket it can block and prevent using the other, so that it is not possible to access the latter socket to prevent connecting another device which may be damaged by contact with the active substances diffused.

Based on the arrangement and construction of the elements referred to and shown in FIG. 1, the assembly is a sandwich-type assembly, so that the components are consecutively assembled on each other by simple movements of robotic arms.

Figure 3:
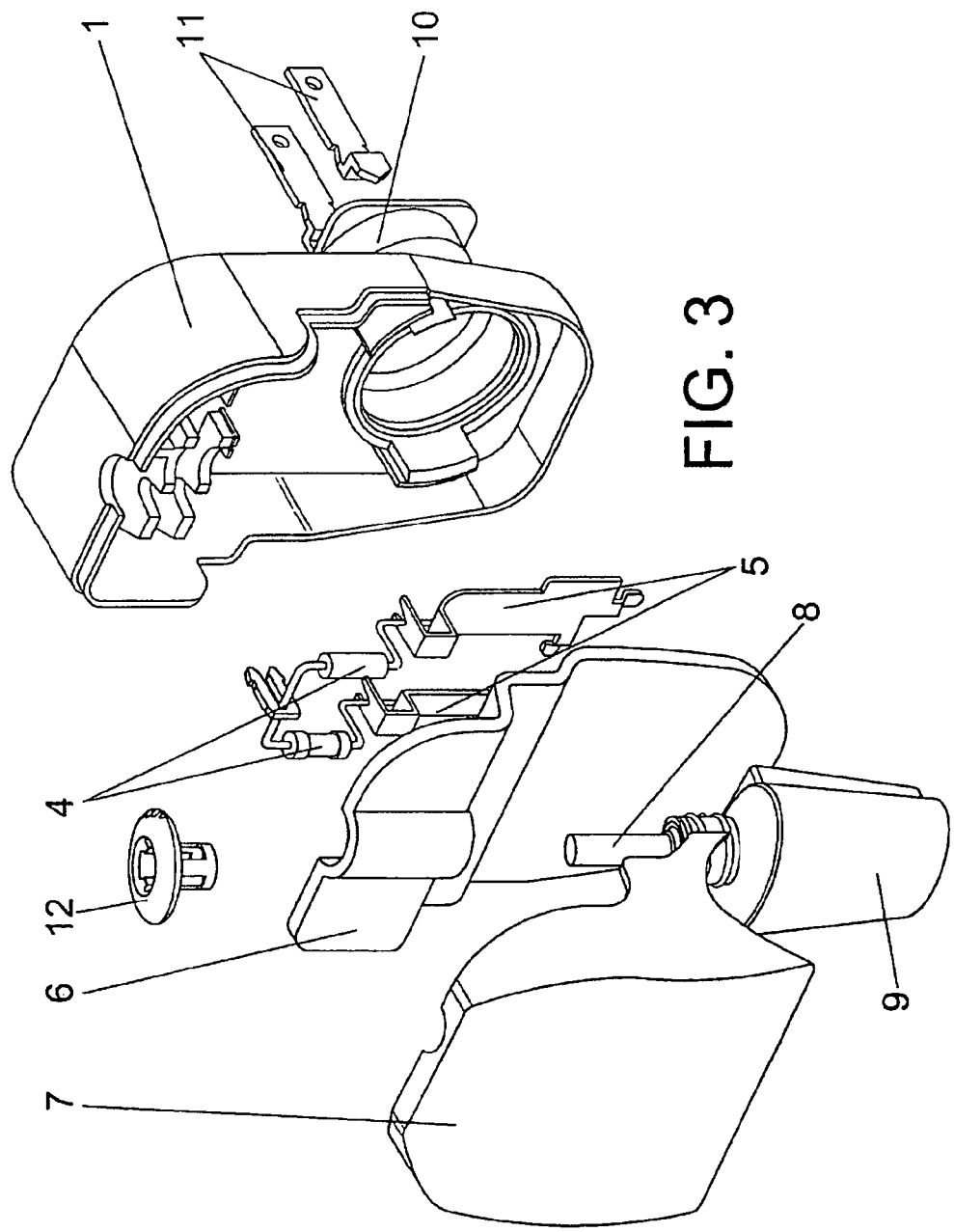
FIG. 3 shows a perspective view similar to that of FIG. 1 without the electronics. In this case the device is only provided with the means allowing to mechanically adjust at will the evaporation intensity.

The described architecture of the device equally allows a configuration incorporating the electronics, this is, the platform or printed circuit (2) with the aforementioned electronic components, and other components meant to allow providing the fragrant substance control functionality as shown in FIG. 1, or one in which the device lacks said electronics incorporating only a manually actuated mechanical component (12) for regulating the evaporation intensity, as shown in FIG. 3, so that in the first case the device will have several functions and performances and in the second the device will have the performance of a conventional device with regulation.

As described before, the electronic means for controlling the diffusion of the active substance, a concept different from regulating the intensity of the emission, allows controlling the diffusion of the fragrance by programming on/off cycles or pulses pre-established by the manufacturer, the user not being able to perceive not manipulate this program, so that the olfactory perception of the user is heightened while preventing the saturation phenomenon and allowing to optimize the fragrance emitted.

Finally, it must be said that the platform or printed circuit board (2), in addition to the components provided on the support (3), such as the electrical resistors or heaters (4) associated to the contacts (5) may incorporate other elements such as a manual on/off button (13) for the device, a light sensor for automatic switching on and off according to the light intensity of the surroundings, an operation indicator, an ornamental lighting for the bottle containing the fragrant liquid, etc.

What is claimed is:

1. Evaporator device for active substances, of the type comprised of a body determining a support base inside which are established the corresponding means to heat a wick emerging from the mouth of a bottle containing fragrant liquid, thereby bearing and thus causing the evaporation of the liquid, all of this with the device connected by a plug on a base, characterized in that it includes a platform or primed circuit (2) with the corresponding electronics for optimizing the diffusion of the fragrance and thereby prevent the phenomenon of olfactory saturation, by means of a program of on/off cycles or pulses pre-established by the manufacturer and which cannot be perceived nor manipulated by the user, such that on said platform or printed circuit (2) with the electronic components is mounted a support (3) for the corresponding hearing elements (4) that are vertically arranged and directly connected to metallic contacts (5) integrated with them in the assembly itself, the corresponding base (1) housing these components being complemented with a closure wall (6) and an exchangeable embellishment case (7).

2. Evaporator device for active substances, according to claim 1, characterized in that from the base (1) containing the platform or printed circuit (2) and the remaining electronic components, as well as being the support (3) for the hearing elements (4) and contacts (5), emerges the corresponding plug (10) with its pins (11) placed in correspondence with the bottom part of said base (1).

3. Evaporator device for active substances, according to claim 1, characterized in that the heating elements (4) consist of corresponding metal oxide resistors integrated in the assembly of the device itself.

4. Evaporator device for active substances, according to claim 1, characterized in that it includes a manually actuated element (12) meant to increase or decrease the intensity of evaporation of the fragrant liquid.

5. An evaporator device for releasing a fragrance from active substances stored in a bottle, the evaporator device composing:

a support base having a plug for connecting to an electrical outlet;

a heating element for directly heating a wick in communication with the active substances, a substantially rigid metallic contact for contacting the plug, the metallic contact being directly connected to the heating element so as to be integral with the heating element;

a primed circuit supported by the support base, the printed circuit having electronics for optimizing a diffusion of the fragrance to prevent olfactory saturation;

a support unit mounted on the printed circuit for supporting the heating element and the metallic contact;

a closure wall separating the bottle; and an exchangeable embellishment case for providing a housing.

6. The evaporator device of claim 5 wherein the plug is disposed in a lower part of the support base.

7. The evaporator device of claim 5 wherein the heating element comprises a metal oxide resistor.

8. The evaporator device of claim 5 further comprising an actuator disposed on the wick for increasing and decreasing an intensity of evaporation of the active substances.

9. An heating assembly for an evaporator device for releasing a fragrance from active substances stored in a bottle, the heating assembly comprising:

a hearing element for heating a wick in communication with the active substances, a substantially rigid metallic contact for contacting a plug, the metallic contact being directly connected to the heating element so as to be integral with the heating element;

a printed circuit having electronics for optimizing a diffusion of the fragrance to prevent olfactory saturation; and a support unit mounted on the printed circuit for supporting the heating element and the metallic contact.

10. The heating assembly of claim 9 wherein the heating element comprises a metal oxide resistor.

* * * * *